(12) United States Patent
Distler et al.

(10) Patent No.: US 6,195,578 B1
(45) Date of Patent: Feb. 27, 2001

(54) MAGNETIC RESONANCE APPARATUS FOR INTRAOPERATIVE IMAGING

(75) Inventors: Peter Distler, Erlangen; Rainer Kuth, Herzogenaurach; Arnulf Oppelt, Spardorf; Theodor Vetter, Erlangen; Herbert Weiler, Alling, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/303,641

(22) Filed: May 3, 1999

(30) Foreign Application Priority Data

Jan. 14, 1999 (DE) .......................................... 299 00 512 U

(51) Int. Cl.$^7$ .................................................. A61B 5/055
(52) U.S. Cl. ..................... 600/415; 324/318; 324/322; 5/601
(58) Field of Search .................................... 600/407, 410, 600/411, 415; 5/601, 607–611; 378/179, 209, 196; 324/318, 322

(56) References Cited

U.S. PATENT DOCUMENTS

| | | | |
|---|---|---|---|
| 4,875,485 | * 10/1989 | Matsutani | 600/415 |
| 4,915,435 | * 4/1990 | Levine | 296/74.1 |
| 5,014,292 | * 5/1991 | Siczek et al. | 378/196 |
| 5,525,905 | * 6/1996 | Mohapatra et al. | 324/318 |
| 5,615,430 | 4/1997 | Nambu et al. . | |
| 5,623,927 | * 4/1997 | Damadian et al. | 324/318 |
| 5,790,996 | * 8/1998 | Narfstrom | 5/610 |
| 5,822,814 | * 10/1998 | Van der Ende | 5/601 |
| 5,842,987 | * 12/1998 | Sahadevan | 600/407 |
| 6,023,799 | * 2/2000 | Wirth et al. | 5/601 |
| 6,094,760 | * 8/2000 | Nonaka et al. | 5/601 |

FOREIGN PATENT DOCUMENTS 92 18 322 U   1/1994  (DE) .
197 36 884    3/1999  (DE) .

* cited by examiner

Primary Examiner—Brian L. Casler
(74) Attorney, Agent, or Firm—Schiff Hardin & Waite

(57) ABSTRACT

A magnetic resonance system with a patient bearing table with an interchangeable-panel receiving mechanism, which table can be used as an operating table. The patient bearing table is mounted at an operating column, which is arranged in front of an insertion end of the magnetic resonance apparatus, such that this table can be swivelled about a vertical axis of rotation.

15 Claims, 2 Drawing Sheets

MAGNETIC RESONANCE APPARATUS FOR INTRAOPERATIVE IMAGING

BACKGROUND OF THE INVENTION

The present invention relates to a magnetic resonance apparatus having a patient bearing table with an interchangeable-panel receiving mechanism. The table can be utilized as an operating table.

Magnetic resonance (MR) apparatuses render sectional images of the human body with high soft-tissue contrast. MR images are used for planning neurosurgical operations. However, the problem arises that the brain shifts in the surgical opening of the skull (brain shift), whereby the operation plan becomes inexact. Given tumors which are imaged in the brain (not metastases), the problem exists that the surgeon usually cannot visually discern the boundaries of the tumor. MR displays these boundaries, for example, based on the destruction of the blood-brain barrier in the case of tumors. This destruction permits the passage of the contrast agent Gd-DTPA. For this reason, magnetic resonance apparatuses are increasingly being employed during the operations in order to correct "brain shift" after the opening of the skull, or to determine if all malignant tissues have been removed following a tumor resection.

Due to their accessibility, for the most part only magnetic resonance apparatuses with relatively low field have been used. However, the achievable image quality is limited here, and the measuring times for a fully anesthetized patient are quite long. What are known as high field magnetic resonance apparatuses with fields above 1 Tesla offer a higher image quality and rather short measuring times, and additional information is available such as functional imaging, perfusion, diffusion and blood flow area. However, such high-field magnetic resonance apparatuses are based on superconductive magnets in which the patient is inserted into a poorly accessible tube. Operations can only be carried out at a face end of the tube under relatively crowded conditions. Working within the magnet system requires a specific expensive operating instrument, which cannot interact with either the magnetic field or with the high-frequency fields. The instrument also must not be influenced by these, and must not itself exert an influence on the magnet system which degrades the imaging.

SUMMARY OF THE INVENTION

It is an object of the present invention to provide a magnetic resonance apparatus that simplifies an operation, and is maximally independent of the magnetic field. It is thus possible to examine the patient in the magnetic resonance apparatus at any time.

To achieve this object, it is inventively provided that the patient bearing table is mounted on an operating column which is arranged before the insertion end of the magnetic resonance apparatus, so as to swivel about a vertical axis of rotation. The mounting preferably occurs such that the operating column is laterally offset relative to the z-axis of the magnet system. The patient bearing table is correspondingly laterally secured beside the operating column so as to be offset relative to the swivelling axis.

The inventive construction of the patient bearing table yields an operating table of high value which is arranged far outside the stray magnetic field of the MR apparatus in an outward position and which can be swivelled directly in front of the insertion opening of the MR apparatus by a simple swivelling of 180°, so that the tabletop, which is constructed as the bed board of the MR apparatus and which is arranged on the operating table in locking fashion, can be pushed into the tube of the MR apparatus for performing corresponding examinations.

The lateral displacement of the operating column relative to the z-axis of the MR system additionally creates the opportunity to use the MR apparatus another way during the operation of a patient in the outward operating position, since the insertion opening of the MR apparatus is then completely free, and another patient can be moved to the apparatus using a trolley or similar device.

The patient bearing table serving as operating table should therein be mounted at the operating column so that it is height-adjustable and/or so that it is tiltable about an axis situated perpendicular to the table's longitudinal axis. This enables an inclination of the operating table, which is frequently appropriate for the respective operating objectives, as well as a height adjustment, which can be freely selected independently of the height of the transport rails for the bed board of the MR apparatus.

According to an additional feature of the present invention, anesthesia equipment can be arranged over the operating column, including an anesthesia device and a monitor, as well as other groups of devices. This not only results in a rather compact operating space, but also has the additional advantage that rather short paths are required for the cable and tubes to the patient.

In order to be able to move the patient even further from the stray field of the MR apparatus and thus to be able to use an inexpensive, commercially available array of operating instruments, it can be provided according to another feature of the present Invention that the operating column can be moved on rails perpendicular to the z-axis of the magnet system in a stoppable manner. This makes it possible to construct an operating room next to the magnetic resonance recording room, separating the operating room by a door, so that during the operation, other patients can be diagnosed with the MR apparatus.

In a particularly advantageous embodiment of an inventive apparatus with an operating room that is separated from the MR recording room, the operating room can form a part of the frame or case of an HF-tight door in the wall between an operating room and a neighboring MR room.

BRIEF DESCRIPTION OF THE DRAWINGS

The features of the present invention which are believed to be novel, are set forth with particularity in the appended claims. The invention, together with further objects and advantages, may best be understood by reference to the following description taken in conjunction with the accompanying drawings, in the several Figures of which like reference numerals identify like elements, and in which:

DESCRIPTION OF THE PREFERRED EMBODIMENTS

Figure 1:
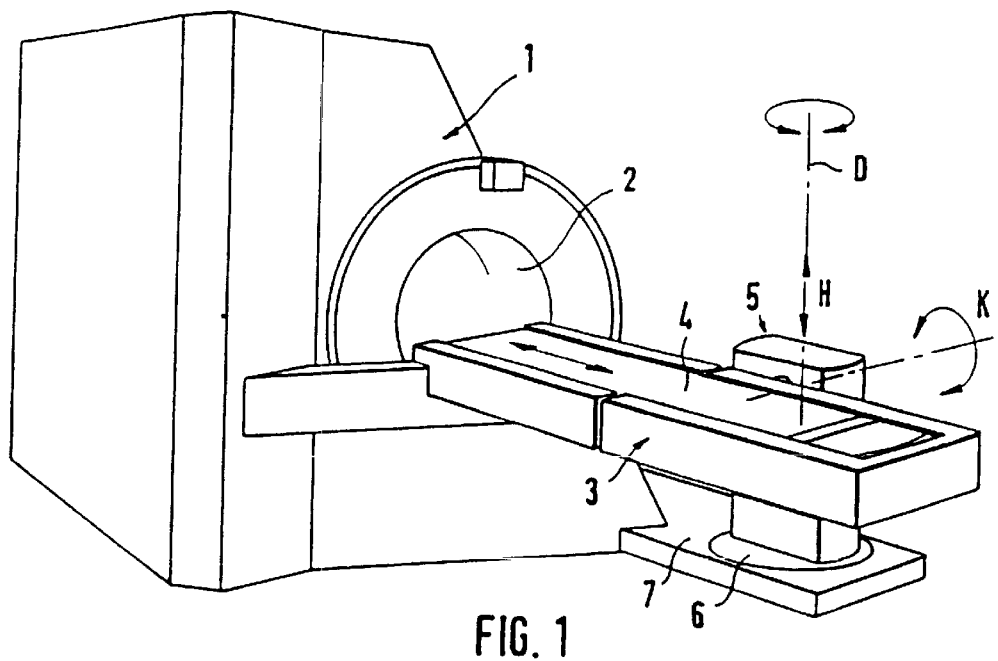
FIG. 1 is a perspective view of an inventive MR apparatus with a swivelling patient bearing table which can be used as an operating table.

FIG. 1 depicts an MR apparatus. In front of a tube 2 of the MR apparatus of a patient bearing table 3 for pushing through a patient is depicted. This patient bearing table is inventively constructed as an operating table, whereby the tabletop 4 is constructed as a bed board for the MR bed, which board can be pushed directly onto the rails of the tube (not depicted). This tabletop 4 for the operating table, which tabletop is constructed as a bed board of the MR bed, can be secured at the patient bearing table 3 by a locking mechanism, which is motorized. The patient bearing table 3 is secured laterally at an operating column 5, which can be rotated about a vertical axis D, such that the patient bearing table 3 can not only be adjusted in height along the lift axis H but can also be swivelled about a tilt axis K which is perpendicular to the longitudinal axis of the table. Both the displacement along the lift axis H and the tilting along the tilt axis K preferably occur via positioning motors that can be moved steplessly. The operating column 5 is supported on a stationary base 7 via the rotatable bearing plate 6. However, instead of this stationary support, it could also be provided that a base can be moved on rails that extend perpendicular to the longitudinal axis of the table depicted in FIG. 1, which corresponds to the z-axis of the magnet system of the magnetic resonance apparatus 1. This allows moving the patient bearing table 3 even further from the stray field of the MR apparatus, even into an operating room adjacent the MR room, for example. But the preferred arrangement is the stationary arrangement depicted in FIG. 1, in which the moving of the patient bearing table 3 from the position of insertion into the MR system into a displaced operating position occurs exclusively by swivelling the operating column 5 about the vertical axis of rotation D.

Figure 2:
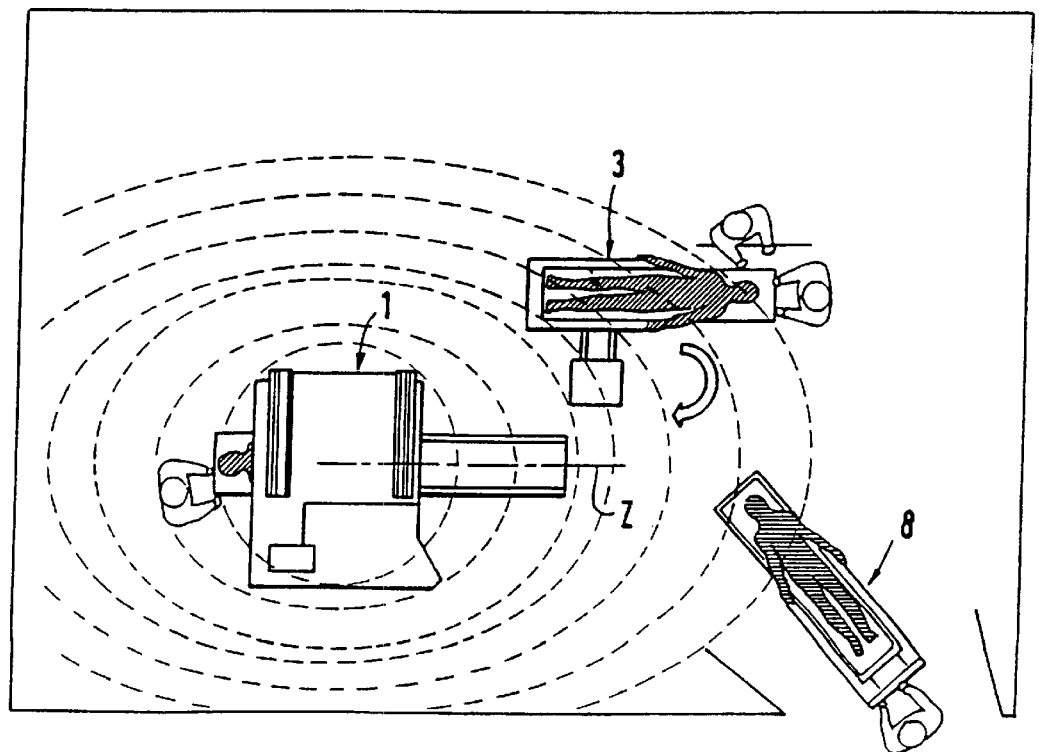
FIG. 2 is a schematic plan view of the arrangement according to FIG. 1 depicting several possibilities for use.

FIG. 2 depicts the position in which the patient bearing table 3 is swivelled 180° from the position in front of the MR apparatus 1, as shown in FIG. 1, into a position in which the patient bearing table 3 is utilized as an operating table. The possibility is evident here, indicated by a patient bearing table that is fashioned as a patient trolley 8, to use the MR apparatus for the simultaneous examination of another patient while the first patient is still lying on the patient bearing table 3 in the operating position. It is additionally indicated in FIG. 2, left, how an intervention at the patient can occur in the stray field of the magnet system on the left side of the MR apparatus. The field lines in FIG. 2 indicate how far the stray magnetic field has already dropped in the out position of the patient bearing table 3 in the operating position, so that operations can also be performed in this position with an inexpensive and commercially available array of operating instruments.

Figure 3:
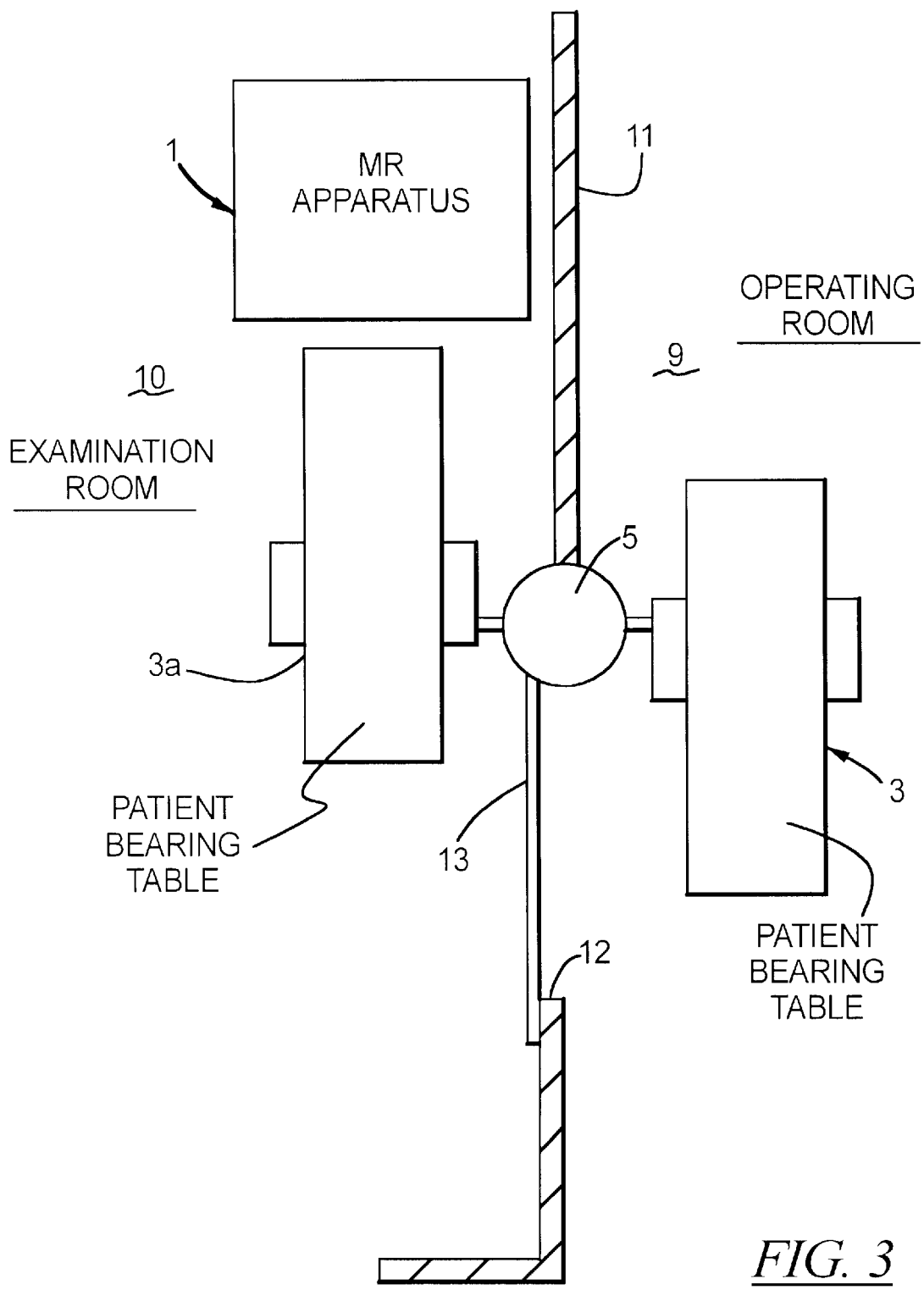
FIG. 3 is a schematic plan view of an apparatus with an adjacent operating room and an MR room and with an operating room built into the door frame of a divider door.

FIG. 3 is a schematic depiction of a modified inventive apparatus in which the operating room 9 and the MR examination room 10 are divided by a high frequency barrier wall 11. A doorway 12 is provided, which can be closed by a high frequency barrier door 13, which is constructed as a sliding door, for example. The operating room 5 forms a part of the door frame between the two rooms 9 and 10, so that the patient bearing table 3 can be swivelled between the measuring position before the MR apparatus 1 and the operating position in the separate operating room 9. In a particularly advantageous manner, this creates the possibility to use the MR apparatus for the examination of additional patients (on bearing table 3a) while the patient on the patient bearing table 3 is operated on in the operating room.

The invention is not limited to the particular details of the apparatus depicted and other modifications and applications are contemplated. Certain other changes may be made in the above described apparatus without departing from the true spirit and scope of the invention herein involved. It is intended, therefore, that the subject matter in the above depiction shall be interpreted as illustrative and not in a limiting sense.

What is claimed is:

1. A magnetic resonance apparatus system, comprising:
   a magnetic resonance apparatus having an insertion end;
   a patient bearing table with an interchangeable-panel receiving mechanism, the table being utilizable as an operating table; and
   the patient bearing table being mounted at an operating column, which is arranged before the insertion end of the magnetic resonance apparatus, such that the table is swivelable about a vertical axis of rotation of the operating column.

2. The magnetic resonance system according to claim 1, wherein the operating column is arranged laterally offset in relation to a z-axis of a magnet system of the magnetic resonance apparatus, and wherein the patient bearing table is secured laterally at the operating column so as to be correspondingly offset relative to the axis of rotation.

3. The magnetic resonance system according to claim 1, wherein the operating table is mounted at the operating column such that a height of the table is adjustable and/or the table is tiltable about an axis that is perpendicular to a table axis of the table.

4. The magnetic resonance system according to claim 1, wherein the system further comprises anesthesia equipment, positioned substantially over the operating column, the anesthesia equipment having an anesthesia device and a monitor.

5. The magnetic resonance system according to claim 1, wherein the operating column is movable and positionable on rails perpendicular to the z-axis of a magnet system of the magnetic resonance apparatus.

6. The magnetic resonance system according to claim 1, wherein the operating column forms a part of a frame of a high frequency barrier door in a wall between an operating room and an adjacent examination space having the magnetic resonance apparatus.

7. A magnetic resonance system, comprising:
   a magnetic resonance apparatus having an insertion end and having a magnetic system;
   a patient bearing table with an interchangeable-panel receiving mechanism, which table being utilizable utilized as an operating table;
   an operating column on which is mounted a patient bearing table, the table being swivelable about a vertical axis of the operating column such that the table is positionable before the insertion end of the magnetic resonance apparatus;

the operating column arranged laterally offset in relation to a z-axis of the magnet system; and the patient bearing table secured laterally at the operating column so as to be correspondingly offset relative to the vertical axis of the operating column.

8. The magnetic resonance system according to claim 7, wherein the operating table is mounted at the operating column such that a height of the table is adjustable and such that the table is tiltable about an axis perpendicular to a table axis of the table.

9. The magnetic resonance system according to claim 1, wherein the system further comprises anesthesia equipment positioned substantially over the operating column, the anesthesia equipment having an anesthesia device and a monitor.

10. The magnetic resonance system according to claim 1, wherein the system further comprises rails for moving and positioning the operating column.

11. The magnetic resonance system according to claim 1, wherein the operating column forms a part of a frame of a high frequency barrier door in a wall between an operating room and an adjacent magnetic resonance examination space that contains the magnetic resonance apparatus.

12. A magnetic resonance system, comprising:

an operating room connected to a magnetic resonance examination room via a wall having a door, said wall and door forming a barrier to high frequency radiation;

an operating column that forms a part of a frame for the door in the wall;

a patient bearing table attached to said operating column and at least swivelable about said operating column such that said table is movable between said operating room and said examination room; and said examination room containing a magnetic resonance apparatus having an insertion end, said table being positionable before said insertion end.

13. The magnetic resonance system according to claim 12, wherein the operating column is arranged laterally offset in relation to a z-axis of a magnet system, of the magnetic resonance apparatus and wherein the patient bearing table is secured laterally at the operating column so as to be correspondingly offset relative to an axis of rotation about the operating column.

14. The magnetic resonance system according to claim 12, wherein the operating table is mounted at the operating column such that a height of the table is adjustable and such that the table is tiltable about an axis perpendicular to a table axis of the table.

15. The magnetic resonance system according to claim 12, wherein the system further comprises anesthesia equipment positioned over the operating column, the anesthesia equipment having an anesthesia device and a monitor.

* * * * *